United States Patent
Annoni et al.

(10) Patent No.: US 10,729,905 B2
(45) Date of Patent: Aug. 4, 2020

(54) PAIN MANAGEMENT BASED ON MUSCLE TENSION MEASUREMENTS

(71) Applicant: Boston Scientific Neuromodulation Corporation, Valencia, CA (US)

(72) Inventors: Elizabeth Mary Annoni, White Bear Lake, MN (US); Jianwen Gu, Valencia, CA (US); Pramodsingh Hirasingh Thakur, Woodbury, MN (US); Bryan Allen Clark, Forest Lake, MN (US); Kyle Harish Srivastava, Saint Paul, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 281 days.

(21) Appl. No.: 15/867,767

(22) Filed: Jan. 11, 2018

(65) Prior Publication Data

US 2018/0193644 A1   Jul. 12, 2018

Related U.S. Application Data

(60) Provisional application No. 62/445,092, filed on Jan. 11, 2017.

(51) Int. Cl.
*A61N 1/00* (2006.01)
*A61N 1/36* (2006.01)
(Continued)

(52) U.S. Cl.
CPC ........ *A61N 1/36071* (2013.01); *A61B 5/4824* (2013.01); *A61B 5/4836* (2013.01); (Continued)

(58) Field of Classification Search
CPC ............ A61N 1/36071; A61N 1/37264; A61N 1/0534; A61N 1/37247; A61N 1/0551; (Continued)

(56) References Cited

U.S. PATENT DOCUMENTS

| 5,774,591 A | 6/1998 | Black et al. |
| 6,076,011 A | 6/2000 | Hoover |

(Continued)

FOREIGN PATENT DOCUMENTS

| RU | 2559783 C1 | 8/2015 |
| WO | WO-2009055127 A1 | 4/2009 |

(Continued)

OTHER PUBLICATIONS

"2015 Sleep in America® Poll Sleep and Pain—Summary of Findings", National Sleep Foundation, (2015), 1-54.

(Continued)

*Primary Examiner* — Mallika D Fairchild
(74) *Attorney, Agent, or Firm* — Schwegman Lundberg & Woessner, P.A.

(57) ABSTRACT

This document discusses, among other things, systems and methods for managing pain of a subject. A system may include one or more sensors configured to sense a signal indicative of muscle electrical or mechanical activity at a specific body location. The muscle electrical or mechanical activity signal may include an electromyography or a mechanical contraction signal. A pain analyzer circuit may extract from the sensed signal one or more signal metrics indicative of muscle tension, and generate a pain score using the signal metrics. The pain score may be output to a user or a process. The system may include a neurostimulator that can adaptively control the delivery of pain therapy by automatically adjusting stimulation parameters based on the pain score.

20 Claims, 4 Drawing Sheets

(51) Int. Cl.
*A61B 5/00* (2006.01)
*A61N 1/372* (2006.01)
*A61N 1/05* (2006.01)
*A61B 5/11* (2006.01)
*A61B 5/0488* (2006.01)

(52) U.S. Cl.
CPC ......... *A61N 1/0534* (2013.01); *A61N 1/0551* (2013.01); *A61N 1/36062* (2017.08); *A61N 1/36139* (2013.01); *A61N 1/37247* (2013.01); *A61N 1/37264* (2013.01); *A61B 5/0488* (2013.01); *A61B 5/1107* (2013.01); *A61N 1/37217* (2013.01)

(58) Field of Classification Search
CPC ............ A61N 1/36139; A61N 1/36062; A61N 1/37217; A61B 5/4836; A61B 5/4824; A61B 5/0036; A61B 5/0488; A61B 5/1107
See application file for complete search history.

(56) References Cited

U.S. PATENT DOCUMENTS

| | | | |
|---|---|---|---|
| 6,088,040 | A | 7/2000 | Oda et al. |
| 6,173,260 | B1 | 1/2001 | Slaney |
| 6,480,734 | B1 | 11/2002 | Zhang et al. |
| 6,659,968 | B1 | 12/2003 | McClure |
| 6,871,099 | B1 | 3/2005 | Whitehurst et al. |
| 7,001,337 | B2 | 2/2006 | Dekker |
| 7,004,907 | B2 | 2/2006 | Banet et al. |
| 7,177,686 | B1 | 2/2007 | Turcott |
| 7,222,075 | B2 | 5/2007 | Petrushin |
| 7,299,086 | B2 | 11/2007 | McCabe et al. |
| 7,376,457 | B2 | 5/2008 | Ross |
| 7,407,485 | B2 | 8/2008 | Huiku |
| 7,463,927 | B1* | 12/2008 | Chaouat ............. A61N 1/36071 607/46 |
| 7,566,308 | B2 | 7/2009 | Stahmann |
| 7,627,475 | B2 | 12/2009 | Petrushin |
| 7,636,602 | B2 | 12/2009 | Baru Fassio et al. |
| 7,650,184 | B2 | 1/2010 | Walter |
| 7,678,061 | B2 | 3/2010 | Lee et al. |
| 7,957,809 | B2 | 6/2011 | Bourget et al. |
| 7,986,991 | B2 | 7/2011 | Prichep |
| 8,019,439 | B2 | 9/2011 | Kuzma et al. |
| 8,209,182 | B2 | 6/2012 | Narayanan |
| 8,398,556 | B2 | 3/2013 | Sethi et al. |
| 8,447,401 | B2 | 5/2013 | Miesel et al. |
| 8,475,370 | B2 | 7/2013 | McCombie et al. |
| 8,529,459 | B2 | 9/2013 | Malker et al. |
| 8,688,221 | B2 | 4/2014 | Miesel |
| 8,744,587 | B2 | 6/2014 | Miesel et al. |
| 8,805,518 | B2 | 8/2014 | King et al. |
| 9,066,659 | B2 | 6/2015 | Thakur et al. |
| 9,119,965 | B2 | 9/2015 | Xi et al. |
| 2004/0015091 | A1 | 1/2004 | Greenwald et al. |
| 2007/0167859 | A1 | 7/2007 | Finneran et al. |
| 2008/0249430 | A1 | 10/2008 | John et al. |
| 2009/0312663 | A1 | 12/2009 | John et al. |
| 2009/0318986 | A1 | 12/2009 | Alo et al. |
| 2010/0016913 | A1 | 1/2010 | Arcot-Krishnamurthy et al. |
| 2010/0286549 | A1 | 11/2010 | John et al. |
| 2011/0021928 | A1 | 1/2011 | Giovangrandi et al. |
| 2011/0137134 | A1 | 6/2011 | Hemmerling et al. |
| 2011/0172562 | A1 | 7/2011 | Sahasrabudhe et al. |
| 2011/0224749 | A1 | 9/2011 | Ben-David et al. |
| 2011/0306846 | A1 | 12/2011 | Osorio |
| 2012/0109012 | A1* | 5/2012 | Cinbis .................. A61B 5/1076 600/587 |
| 2013/0165994 | A1 | 6/2013 | Ternes et al. |
| 2013/0268016 | A1 | 10/2013 | Xi et al. |
| 2014/0276188 | A1 | 9/2014 | Jardin |
| 2014/0276549 | A1* | 9/2014 | Osorio ................ A61M 5/1723 604/503 |
| 2016/0129272 | A1 | 5/2016 | Hou et al. |
| 2016/0243359 | A1 | 8/2016 | Sharma |
| 2017/0136264 | A1* | 5/2017 | Hyde ........................ A61N 7/00 |
| 2017/0165485 | A1* | 6/2017 | Sullivan ............ A61N 1/36021 |
| 2018/0085055 | A1 | 3/2018 | Annoni et al. |
| 2018/0085584 | A1 | 3/2018 | Thakur et al. |
| 2018/0110464 | A1 | 4/2018 | Annoni et al. |

FOREIGN PATENT DOCUMENTS

| | | |
|---|---|---|
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2015060888 A1 | 4/2015 |
| WO | WO-2015128567 | 9/2015 |
| WO | WO-2016077786 A1 | 5/2016 |

OTHER PUBLICATIONS

"International Application Serial No. PCT/US2017/048867, International Search Report dated Nov. 13, 2017", 5 pgs.
"International Application Serial No. PCT/US2017/048867, Written Opinion dated Nov. 13, 2017", 6 pgs.
"International Application Serial No. PCT/US2017/048896, International Search Report dated Nov. 27, 2017", 5 pgs.
"International Application Serial No. PCT/US2017/048896, Written Opinion dated Nov. 27, 2017", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and

(56) References Cited

OTHER PUBLICATIONS

Personal Monitoring", The Scientific World Journal, vol. 2014 Article ID 190824, (2014), 11 pgs.

Bansevicius, Dalius, et al., "Mental stress of long duration: EMG activity, perceived tension, fatigue, and pain development in pain-free subjects", Headache: The Journal of Head and Face Pain; 37.8, (1997), 499-510.

Barad, Meredith J., et al., "Complex Regional Pain Syndrome Is Associated With Structural Abnormalities in Pain-Related Regions of the Human Brain", The Journal of Pain, vol. 15, No. 2, (Feb. 2914), 197-203.

Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.

Bartlett, Marian Stewart, et al., "Automatic Decoding of Facial Movements Reveals Deceptive Pain Expressions", Current Biology 24, 738-743, Mar. 31, 2014.

Beneck, George J., et al., "Spectral analysis of EMG using intramuscular electrodes reveals non-linear fatigability characteristics in persons with chronic low back pain", Journal of Electromyography and Kinesiology 23, (2013), 70-77.

Ben-Israel, Nir, et al., "Monitoring the nociception level: a multi-parameter approach", J Clin Monit Comput, (Jul. 2012), 10 pgs.

Ben-Israel, Nir, et al., "Monitoring the nociception level: a multi-parameter approach", J Clin Monit Comput 27, (2013), 659-668.

Boselli, E., et al., "Prediction of immediate postoperative pain using the analgesia/nociception index: a prospective observational study", British Journal of Anaesthesia 112 (4):, (2014), 715-721.

Boselli, E., et al., "Prospective observational study of the non-invasive assessment of immediate postoperative pain using the analgesia/nociception index (ANI)", British Journal of Anaesthesia 111, (2013), 453-459.

Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.

Chan, C. W.Y., et al., "Subjective pain sensation is linearly correlated with the Flexion reflex in man", Brain Research, 479, (1989), 145-150.

Chapman, C. Richard, et al., "Phasic pupil dilation response to noxious stimulation in normal volunteers: relationship to brain evoked potentials and pain report", (1999), 44-52.

Chen, Shuzhen, et al., "The role of the autonomic nervous system in hypertension: a bond graph model study", Physiological measurement 29.4 (2008): 473, (2008), 473-495.

Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013 (2013), 1-10.

Chuang, Chiung-Cheng, et al., "Photoplethysmography variability as an alternative approach to obtain heart rate variability information in chronic pain patient", J Clin Monit Comput—Published online, (Feb. 24, 2015), 1-6.

Chung, OK Y., "Baroreflex sensitivity associated hypoalgesia in healthy states is altered by chronic pain", Pain 138, (2008), 87-97.

Ciampi De Andrade, Daniel, et al., "Neurophysiological assessment of spinal cord stimulation in failed back surgery syndrome", Pain 150, (2010), 485-491.

Cinaz, Burcu, et al., "Monitoring of mental workload levels during an everyday life office-work scenario", Pers Ubiquit Comput 17, (2013), 229-239.

Clark, Bryan Allen, et al., "Pain Management Based on Functional Measurements", U.S. Appl. No. 62/445,075, filed Jan. 11, 2017.

Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.

Dansie, Elizabeth J., et al., "Activity in Adults with Chronic Widespread Pain", The Journal of Pain—Accepted Manuscript, (2014), 33 pgs.

Davydov, Dmitry M., et al., "Cardiovascular activity and chronic pain severity", Physiology & Behavior 152, 203-216 (2015).

De-La-Herran, Alvaro M., et al., "Gait Analysis Methods: An Overview of Wearable and Non-Wearable Systems, Highlighting Clinical Applications", Sensors 14, (2014), 3362-3394.

Denk, Franziska, et al., "Chronic Pain: Emerging Evidence for the Involvement of Epigenetics", Neuron 73 (3), (2012), 435-444.

Duschek, S., "Relationship between baroreceptor cardiac reflex sensitivity and pain experience in normotensive individuals", International Journal of Psychophysiology 65, (2007), 193-200.

Eisenberg, Elon, et al., "Quantitative Sensory Testing for Spinal Cord Stimulation in Patients With Chronic Neuropathic Pain", (2006), 161-165.

Elgendi, Mohamed, "On the analysis of fingertip photoplethysmogram signals", Current cardiology reviews 8.1, (2012), 14-25.

Evans, Subhadr, et al., "Heart rate variability as a biomarker for autonomic nervous system response differences between children with chronic pain and healthy control children", Journal of Pain Research 3.6, (2013), 449-457.

Fagius, J., et al., "The cold pressor test: effects on sympathetic nerve activity in human muscle and skin nerve fascicles", Acta physiologica Scandinavica 137.3, (1989), 325-334.

Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.

Frederiks, Joost, et al., "Within-subject electrocardiographic differences at equal heart rates: role of the autonomic nervous system", Pflugers Archiv 441.5, (2001), 717-724.

Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).

Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.

Gesche, Heiko, et al., "Continuous blood pressure measurement by using the pulse transit time: comparison to a cuff-based method", European journal of applied physiology 112.1, (2012), 309-315.

Godfrey, A., et al., "Direct measurement of human movement by accelerometry", Medical Engineering & Physics 30 (2008) 1364-1386.

Godfrey, A., et al., "Instrumenting gait with an accelerometer: a system and algorithm examination", Medical Engineering & Physics, Mar. 2015, doi:10.1016/j.medengphy.2015.02.003, 24 pgs.

Gouveia, S., et al., "Assessing Baroreflex Sensitivity in the Sequences Technique: Local versus Global Approach", Computers in Cardiology, 32, (2005), 279-282.

Granovsky, Yelena, et al., "Objective Correlate of Subjective Pain Perception by Contact Heat-Evoked Potentials", The Journal of Pain, vol. 9, No. 1, (Jan. 2008), 53-63.

Green, Alexande L., "Measurement of muscle sympathetic nerve activity reveals true sympathetic changes in chronic pain", Exp Physiol 97.10, (2012), 1083.

Hallman, David, et al., "Autonomic regulation, physical activity and perceived stress in subjects with musculoskeletal pain: 24-hour ambulatory monitoring", International Journal of Psychophysiology 86, (2012), 276-282.

Hallman, David M., et al., "Changes in physical activity and heart rate variability in chronic neck-shoulder pain: monitoring during work and leisure time", Int Arch Occup Environ Health 87, (2014), 735-744.

Hallman, David M., et al., "Long-Term Monitoring of Physical Behavior Reveals Different Cardiac Responses to Physical Activity among Subjects with and without Chronic Neck Pain", BioMed

(56) References Cited

OTHER PUBLICATIONS

Research International, vol. 2015, Article ID 907482, 11 pages, http://dx.doi.org/10.1155/2015/907482, 11 pages.
Hartwich, Doreen, et al., "Effect of muscle metaboreflex activation on spontaneous cardiac baroreflex sensitivity during exercise in humans", J Physiol 589.24, (2011), 6157-6171.
Jensen, MP, et al., "Brain Eeg activity correlates of chronic pain in persons with spinal cord injury: clinical implications", Nature; Spinal Cord; 51, (Jul. 17, 2012), 55-58.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.
Keefe, Francis J,, et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", SPINE, vol. 13, No. 3, (2008), 312-317.
Kim, Young UK, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", SPINE, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule of Skin Resistance Responses", Psychophysiology, vol. 18, No. 3, (May 1981), 268-270.
Littlewort, Gwen C., et al., "Automatic Coding of Facial Expressions Displayed During Posed and Genuine Pain", Image and Vision Computing, 27(12) p. 1741-1844.

Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
March, Antonio, et al., "Pain Biomarkers", Clin Drug Invest, 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C et al., "Quantitative sensory testing in the German Research Network on Neuropathic Pain (DFNS): Somatosensory abnormalities in 1236 patients with different neuropathic pain syndromes", Pain 150, (2010), 439-450.
McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
McCracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Mylius, Vett, et al., "Sex differences in nociceptive withdrawal reflex and pain perception", Somatosensory and Motor Research 22 (3), (Sep. 2005), 207-211.
Neblett, Randy, et al., "What Is the Best Surface Emg Measure of Lumbar Flexion-Relation for Distinguishing Chronic Low Back Pain Patients From Pain-Free Controls?", Clin J Pain 29 (4)—NIH Public Access, (Apr. 2013), 334-340.
NG, Joseph, et al., "EMG activity of trunk muscles and torque output during isometric axial rotation exertion: a comparison between back pain patients and matched controls", Journal of Orthopaedic Research; 20, (2002), 112-121.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE |DOI:10.1371/journal.pone.0149085 Feb. 25, 2016, 27 pgs.

(56) References Cited

OTHER PUBLICATIONS

Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.

Pleger, Burkhard, et al., "Patterns of cortical reorginization parallel impaired tactile discrimination and pain intensity in complex regional pain syndrome", NeuroImage 32, (2006), 503-510.

Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.

Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.

Prichep, Leslie S., et al., "Evaluation of the Pain Matrix Using EEG Source Localization: A Feasibility Study", Pain Medicine 12, (2011), 1241-1248.

Prkachin, Kenneth, "The consistency of facial expressions of pain: a comparison across modalities", Pain, 51, (1992), 279-306.

Raminen, Tina, et al., "The Impact of Spinal Cord Stimulation on Sleep Patterns", Neuromodulation 19, (2016), 477-481.

Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.

Rhudy, Jamie L., et al., "Defining the nociceptive flexion reflex (NFR) threshold in human participants: A comparison of different scoring criteria", Pain 128, (2007), 244-253.

Roy, Sourav Dey, et al., "An Approach for Automatic Pain Detection through Facial Expression", Procedia Computer Science 84 (2016) 99-106.

Sacco, Marcella, et al., "The Relationship Between Blood Pressure and Pain", The Journal of Clinical Hypertension vol. 15, No. 8, (Aug. 2013), 600-605.

Sarnthein, Johannes, et al., "Increased EEG power and slowed dominant frequncy in patients with neurogenic pain", Brain 129, (2005), 55-64.

Sato, Karina L/, et al., "Spinal Cord Stimulation (SCS) Improves Decreased Physical Activity Induced by Nerve Injury", Behavioral Neuroscience, vol. 128, No. 5, (2914), 625-632.

Sawada, Yukihiro, et al., "Normalized pulse volume (NPV) derived photo-plethysmography as a more valid measure of the finger vascular tone", International Journal of Psychophysiology 41, (2001), 1-10.

Sayar, Kemal, et al., "Sleep Quality in Chronic Pain Patients", Can J. Psychiatry, vol. 47, No. 9, (Nov. 2002), 844-848.

Schulman, Joshua J., et al., "Thalamocortical dysrhythmia syndrome: MEG imaging of neuropathic pain", (Jul. 25, 2014), 33-39.

Schulz, Enrico, et al., "Prefrontal Gamma Oscillations Encode Tonic Pain in Humans", Cerebral Cortex 2015, (Mar. 8, 2015), 1-8.

Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.

Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.

Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.

Sihvonen, T., et al., "Electric behavior of low back muscles during lumbar pelvic rhythm in low back pain patients and healthy controls", Archives of physical medicine and rehabilitation; 72.13, (1991), 1080-1087.

Simoes, Mario A., "Feasibility of Wearable Sensors to Determine Gait Parameters", University of South Florida Scholar Commons, (2011), 1-98.

Skljarevski, V., et al., "The nociceptive flexion reflex in humans—review article", Pain, 96, (2002), 3-8.

Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

Srivastava, Kyle Harish, et al., "Pain Management Based on Cardiovascular Parameters", U.S. Appl. No. 62/445,053, filed Jan. 11, 2017.

Srivastava, Kyle Harish, et al., "Pain Management Based on Emotional Expression Measurements", U.S. Appl. No. 62/445,082, filed Jan. 11, 2017.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behav. Med. 21, (2014), 961-965.

Swenne, C. A., "Baroreflex sensitivity: mechanisms and measurement", Neth Heart J 21, (2013), 58-60.

Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.

Tagliazucchi, Enzo, et al., "Brain resting state is disrupted in chronic back pain patients", Neurosci Lett. 485 (1)—NIH Public Access, (Nov. 12, 2010), 26-31.

Tao, Weijun, et al., "Gait Analysis Using Wearable Sensors", Sensors 12, (2012), 2255-2283.

Tauda, Makoto, et al., "P2X4receptorsandneuropathicpain", Frontiers in Cellular Neuroscience, vol. 7, Article 191, (Oct. 28, 2013), 1-6.

Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.

Thakur, Pramodsingh Hirasingh, et al., "Method and Apparatus for Pain Control Using Baroreflex Sensitivity During Posture Change", U.S. Appl. No. 62/412,587, filed Oct. 25, 2016.

Thakur, Pramodsingh Hirasingh, et al., "Systems and Methods for Closed-Loop Pain Management", U.S. Appl. No. 62/400,313, filed Sep. 27, 2016.

Thankur, Pramodsingh Hirasingh, et al., "Method and Apparatus for Pain Management Using Heart Sounds", U.S. Appl. No. 62/395,641, filed Sep. 16, 2016.

Theuvenel, Peter J., et al., "Responses to Median and Tbial Nerve Stimulation in Patients with Chronic Neuropathic Pain", Brain Topography, vol. 11, No. 4, (1999), 306-313.

Uceyler, Nuncan, et al., "Differential expression of cytokines in painful and painless neuropathies", (2007).

Uzar, E., et al., "Serum cytokine and pro-brain natriuretic peptide (BNP) levels in patients with migraine", European Review for Medical and Pharmacological Sciences; 15, (2011), 1111-1116.

Van Velzen, Marit H.N., et al., "Effect of heat-induced pain stimuli on pulse transit time and pulse wave amplitude in healthy volunteers", Physiological Measurement 37, (2016), 52-66.

Villarejo, Viqueira Maria, et al., "A Stress Sensor Based on Galvanic Skin Response (GSR) Controlled by ZigBee", Sensors 12, (2012), 6075-6101.

Walton, K. D., et al., "Abnormal thalamocortical activity in patients with Complex Regional Pain Syndrome (CRPS) Type 1", Pain 150, (2010), 41-51.

Willer, Jean Claude, "Comparative Study of Perceived Pain and Nociceptive Flexion Reflex in Man", Pain, 3, (1977), 69-80.

Williams, Dewayne P., et al., "Effects of Chronic Pelvic Pain on Heart Rate Variability in Women", The Journal of Urology, vol. 194,, (Nov. 2015), 1-6.

(56) References Cited

OTHER PUBLICATIONS

Wong, Arnold Y.L., et al., "Does experimental low back pain change posteroanterior lumbar spinal stiffness and trunk muscle activity? A randomized crossover study", Clinical Biomechanics 34, (2016), 45-52.

Wong, Jih-Sen, et al., "A comparative study of pulse rate variability and heart rate variability in healthy subjects", J Clin Monit Comput 26, (2012), 107-114.

Wu, Hao-Yu, et al., "Eulerian Video Magnification for Revealing Subtle Changes in the World", ACM Transactions on Graphics 31, No. 4, (Jul. 1, 2012), 1-8.

Zamuner, Antonio R., et al., "Respiratory Sinus Arrhythmia and its Association with Pain in Women with Fibromyalgia Syndrome", Pain Practice, vol. 16, Issue 6, (2016), 704-711.

Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.

Zeng, Zhihong, et al., "A Survey of Affect Recognition Methods: Audio, Visual and Spontaneous Expressions", ICMI'07, Nov. 12-15, 2007, 126-133.

Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.

Zhou, Jing, et al., "Recurrent Convolutional Neural Network Regression for Continuous Pain Intensity Estimation in Video", arXiv preprint arXiv:1605.00894 (2016) 84-92.

Zhou, Jing, et al., "Recurrent Convolutional Neural Network Regression for Continuous Pain Intensity Estimation in Video", Technical Report, (May 3, 2016), 1-11.

\* cited by examiner

PAIN MANAGEMENT BASED ON MUSCLE TENSION MEASUREMENTS

CLAIM OF PRIORITY

This application claims the benefit of priority under 35 U.S.C. § 119(e) of U.S. Provisional Patent Application Ser. No. 62/445,092, filed on Jan. 11, 2017, which is herein incorporated by reference in its entirety.

CROSS REFERENCE TO RELATED APPLICATIONS

This application is related to commonly assigned U.S. Provisional Patent Application Ser. No. 62/445,053, entitled "PAIN MANAGEMENT USING CARDIOVASCULAR PARAMETERS", filed on Jan. 11, 2017, U.S. Provisional Patent Application Ser. No. 62/445,061, entitled "PAIN MANAGEMENT BASED ON BRAIN ACTIVITY MONITORING", filed on Jan. 11, 2017, U.S. Provisional Patent Application Ser. No. 62/445,069, entitled "PAIN MANAGEMENT BASED ON RESPIRATION-MEDIATED HEART RATES", filed on Jan. 11, 2017, U.S. Provisional Patent Application Ser. No. 62/445,075, entitled "PAIN MANAGEMENT BASED ON FUNCTIONAL MEASUREMENTS", filed on Jan. 11, 2017, U.S. Provisional Patent Application Ser. No. 62/445,082, entitled "PAIN MANAGEMENT BASED ON EMOTIONAL EXPRESSION MEASUREMENTS", filed on Jan. 11, 2017, U.S. Provisional Patent Application Ser. No. 62/445,095, entitled "PATIENT-SPECIFIC CALIBRATION OF PAIN QUANTIFICATION", filed on Jan. 11, 2017, U.S. Provisional Patent Application Ser. No. 62/395,641, entitled "METHOD AND APPARATUS FOR PAIN MANAGEMENT USING HEART SOUNDS", filed on Sep. 16, 2016, U.S. Provisional Patent Application Ser. No. 62/400,313, entitled "SYSTEMS AND METHODS FOR CLOSED-LOOP PAIN MANAGEMENT", filed on Sep. 27, 2016, U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, U.S. Provisional Patent Application Ser. No. 62/412,587, entitled "METHOD AND APPARATUS FOR PAIN CONTROL USING BAROREFLEX SENSITIVITY DURING POSTURE CHANGE", filed on Oct. 25, 2016, which are incorporated by reference in their entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient's spinal cord, such as particular spinal nerve roots or nerve bundles, to create an analgesic effect that masks pain sensation.

SUMMARY

By way of example, chronic pain management may involve determining appropriate treatment regimens such as SCS and evaluating therapy efficacy. Accurate pain assessment and characterization are desirable for managing patients with chronic pain. Currently, pain assessment generally relies on patient subjective report of pain symptoms, including severity, pattern, or duration of pain. Based on the patient reported pain sensation, a clinician may prescribe a pain therapy, such as to manually program an electrostimulator for delivering a neuromodulation therapy. However, the subjective description of pain sensation may be constrained by patient cognitive abilities. The subjective pain description may also be subject to intra-patient variation, such as due to a progression of a chronic disease, or a change in general health status or medication. Having a patient to report and describe each pain episode he or she has experienced is not efficient and may delay appropriate pain therapy. Additionally, for patients in an ambulatory setting who lack immediate access to medical assistance, manual adjustment of pain therapy by a clinician may not be feasible especially if immediate therapy titration is required. The present inventors have recognized that there remains a demand for improving pain management, such as systems and methods for objective pain assessment and automated closed-loop pain therapy based on objective pain assessment.

This document discusses, among other things, systems, devices, and methods for assessing pain in a subject. The system includes one or more sensors configured to sense from the subject a signal indicative of muscle electrical or mechanical activity at a specific body location. The electrical or mechanical activity signal may include an electromyography (EMG) or a mechanical contraction signal. One or more signal metrics indicative of muscle tension may be extracted from the sensed muscle electrical or mechanical activity signal. A pain analyzer circuit may generate a pain score using the one or more signals metrics. The pain score can be output to a patient, or used in closed-loop control of pain therapy.

Example 1 is a system for managing pain of a patient, the system comprising a sensor circuit, a pain analyzer circuit, and an output unit. The sensor circuit may be coupled to one or more sensors configured to sense from the patient at least one signal indicative of muscle electrical or mechanical activity at a specific body location. The pain analyzer circuit, coupled to the sensor circuit, may be configured to detect muscle tension using one or more signal metrics generated from the sensed at least one signal indicative of a muscle electrical or mechanical activity at the specific body location, the one or more signal metrics indicative of muscle tension, and generate a pain score using the generated one or more signal metrics. The output unit may be configured to output the pain score to a user or a process.

In Example 2, the subject matter of Example 1 optionally includes an electrostimulator configured to generate electrostimulation energy to treat pain, and a controller circuit coupled to the pain analyzer circuit and the electrostimulator. The controller circuit may be configured to control the electrostimulator to deliver a pain therapy and to control the electrostimulation energy generated by the electrostimulator according to the pain score.

In Example 3, the subject matter of Example 2 optionally includes the electrostimulator that may be further configured to deliver at least one of: a spinal cord stimulation; a brain stimulation; or a peripheral nerve stimulation.

In Example 4, the subject matter of any one or more of Examples 2-3 optionally includes the controller circuit that may be further configured to deliver first electrostimulation to the patient in response to the pain score exceeding a threshold value, and to deliver second electrostimulation to the patient in response to the pain score falling below the threshold value. The first and second electrostimulations may differ in at least one of an electrostimulation energy, an electrostimulation pulse shape, or an electrostimulation pattern.

In Example 5, the subject matter of any one or more of Examples 1-4 optionally includes the sensor circuit that may be coupled to an electromyography (EMG) sensor configured to sense an EMG signal at the specific body location.

In Example 6, the subject matter of Example 5 optionally includes the EMG sensor that may be further configured to be positioned at a patient skin area next to a target muscle to record an electrical activity of muscle tension contributing to or affected by patient pain.

In Example 7, the subject matter of any one or more of Examples 5-6 optionally includes the EMG sensor that may be further configured to be positioned on a face of the patient to record an electrical activity of facial muscle tension associated with pain-related emotional distress.

In Example 8, the subject matter of any one or more of Examples 5-7 optionally includes the EMG sensor which may comprise an epidermal sensor configured to be detachably mounted on a skin of the specific body location of the patient.

In Example 9, the subject matter of any one or more of Examples 1-8 optionally include the sensor circuit coupled to a muscle contraction sensor configured to sense a mechanical contraction signal from a muscle at the specific body location of the patient.

In Example 10, the subject matter of Example 9 optionally includes the muscle contraction sensor that may comprise a sonomicrometry crystal configured to record muscle shortening.

In Example 11, the subject matter of any one or more of Examples 1-10 optionally includes the sensor circuit coupled to first and second sensors. The first sensor may be configured to be positioned at a first patient location to sense a first muscle tension signal at one side of a specific muscle, and the second sensor may be configured to be positioned at a second patient location to sense a second muscle tension signal at an opposite side of the specific muscle. The pain analyzer circuit may be further configured to: detect a bilateral asymmetry indicator using first signal metrics generated from the first muscle tension signal and second signal metrics generated from the second muscle tension signal, the bilateral asymmetry indicator indicating asymmetric muscle activities between the one side and the opposite side of the specific muscle; and generate the pain score further using the detected bilateral asymmetry indicator.

In Example 12, the subject matter of any one or more of Examples 1-11 optionally includes the pain analyzer circuit that may be further configured to generate the pain score using a combination of a plurality of the signal metrics weighted by their respective weight factors.

In Example 13, the subject matter of any one or more of Examples 1-12 optionally includes the pain analyzer circuit that may be further configured to generate the pain score using a combination of comparisons between the plurality of the signal metrics and respective threshold values.

In Example 14, the subject matter of any one or more of Examples 1-13 optionally includes the output unit that may be further configured to produce an alert based on the pain score.

In Example 15, the subject matter of any one or more of Examples 2-14 optionally includes an implantable neuromodulator device (IND) that may include one or more of the sensor circuit, the pain analyzer circuit, or the electrostimulator.

Example 16 is a method for managing pain of a patient using an implantable neuromodulator device (IND). The method comprises: sensing at least one signal indicative of muscle electrical or mechanical activity at a specific body location of the patient using one or more sensors; generating, from the sensed at least one signal indicative of muscle electrical or mechanical activity, one or more signal metrics indicative of muscle tension at the specific body location of the patient; detecting a muscle tension using the one or more signal metrics; generating a pain score based on the one or more signal metrics; and outputting the pain score to a user or a process.

In Example 17, the subject matter of Example 16 optionally includes delivering a pain therapy via the IND. The pain therapy may include electrostimulation energy determined according to the pain score.

In Example 18, the subject matter of any one or more of Examples 16-17 optionally includes the muscle tension signal that may include an electromyography (EGM) signal sensed from a patient skin area next to a target muscle. The EMG signal may be indicative of an electrical activity of muscle tension contributing to or affected by patient pain.

In Example 19, the subject matter of any one or more of Examples 16-18 optionally includes the muscle tension signal that may include an EMG signal sensed from a face of the patient. The EMG signal indicative of an electrical activity of facial muscle tension associated with pain-related emotional distress.

In Example 20, the subject matter of any one or more of Examples 16-19 optionally includes the muscle tension signal that may include a mechanical muscle signal sensed from a muscle at the specific body location of the patient.

In Example 21, the subject matter of any one or more of Examples 16-20 optionally includes sensing first and second muscle tension signals via respective first and second sensors. The first muscle tension signal is indicative of a muscle tension at one side of a specific muscle, and the second muscle tension signal is indicative of a muscle a tension at an opposite side of the specific muscle. The muscle tension detection may include detecting a bilateral asymmetry indicator using first signal metrics generated from the first muscle tension signal and second signal metrics generated from the second muscle tension signal. The bilateral asymmetry indicator indicates asymmetric muscle activities between the one side and the opposite side of the specific muscle; and generating the pain score further using the detected bilateral asymmetry indicator.

In Example 22, the subject matter of any one or more of Examples 16-21 optionally includes generating the pain score using a combination of a plurality of the signal metrics weighted by their respective weight factors.

The pain score generated based on the muscle electrical or mechanical activity, such as based on signal metrics indicative of muscle tension as discussed in this document, may improve medical diagnostics of automated characterization of patient pain, as well as individualized therapies to alleviate pain and to reduce side effects. The systems, devices, and methods discussed in this document may also enhance the performance and functionality of a pain management system or device. A device or a system programmed with the sensor-based pain assessment methods can have improved automaticity in medical diagnostics. More efficient device memory or communication bandwidth usage may be achieved by storing or transmitting medical information more relevant to clinical decisions. Additionally, through improved pain therapy based on patient individual need and therapy efficacy, battery longevity of an implantable device may be enhanced, or pain medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
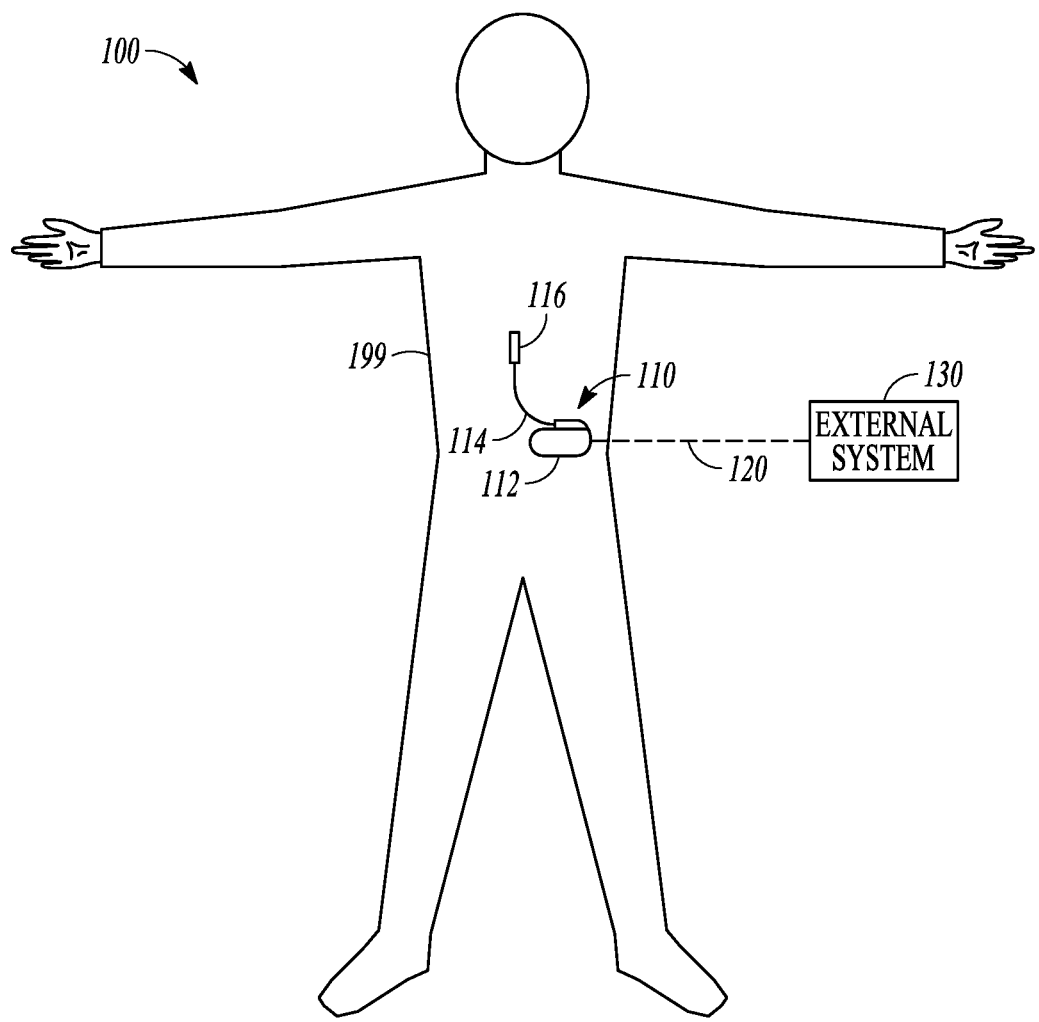
FIG. 1 illustrates, by way of example and not limitation, an example of a neuromodulation system and portions of an environment in which the neuromodulation system may operate.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Clinically, chronic pain may be associated with muscle tension. When muscles remain being contracted for an extended period of time, blood flow to the soft tissues, including muscles, tendons, and nerves in the back may be reduced. The resulting decrease in oxygen and a buildup of biochemical waste in the muscles may cause muscle tension, spasm, and back pain. Muscle tension and stiffness may also contribute to pain in shoulder, neck, upper back, hips, upper and lower legs and feet. Close monitoring of patient muscle tension may provide an objective assessment of pain, and may be used to improve pain therapy efficacy.

Disclosed herein are systems, devices, and methods for or assessing pain in a subject, and optionally programming pain therapy based on the pain assessment. In various embodiments, the present system may include sensors configured to sense a signal indicative of muscle electrical or mechanical activity at a specific body location. The muscle tension signal may include an EMG or a mechanical contraction signal. A pain analyzer circuit may generate a pain score using signal features extracted from the sensed signal, where the signal features are indicative of muscle tension. The system may include a neurostimulator that can adaptively control the delivery of pain therapy by automatically adjusting stimulation parameters based on the pain score.

The present system may be implemented using a combination of hardware and software designed to provide a closed-loop pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, among others. The patient monitoring may include generating recommendations to the patient or a clinician regarding pain treatment.

FIG. 1 illustrates, by way of example and not limitation, an example of a neuromodulation system 100 for managing pain in a subject such as a patient with chronic pain, and portions of an environment in which the neuromodulation system 100 may operate. The neuromodulation system 100 may include an implantable system 110 that may be associated with a body 199 of the subject, and an external system 130 in communication with the implantable system 110 via a communication link 120.

The implantable system 110 may include an ambulatory medical device (AMD), such as an implantable neuromodulator device (IND) 112, a lead system 114, and one or more electrodes 116. The IND 112 may be configured for subcutaneous implant in a patient's chest, abdomen, or other parts of the body 199. The IND 112 may be configured as a monitoring and diagnostic device. The IND 112 may include a hermetically sealed can that houses sensing circuitry to sense physiological or functional signals from the patient via sensing electrodes or ambulatory sensors associated with the patient and in communication with the IND 112. In some examples, the sensing electrodes or the ambulatory sensors may be included within the IND 112. Physiological or functional signals may be sensed during a pain episode. The sensed physiological or functional signals may include at least one signal indicative of muscle electrical or mechanical activity at a specific body location. The IND 112 may generate signal metrics indicative of muscle tension from the sensed muscle electrical or mechanical activity signal, and characterize and quantify the pain, such as to determine onset, intensity, severity, duration, or patterns of the pain experienced by the subject. The IND 112 may generate an alert to indicate occurrence of a pain episode, pain exacerbation, or efficacy of pain therapy, and present the alert to a clinician.

The IND 112 may alternatively be configured as a therapeutic device for treating or alleviating the pain. In addition to pain monitoring circuitry, the IND 112 may further include a therapy unit that can generate and deliver energy or modulation agents to a target tissue. The energy may include electrical, magnetic, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IND 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on implantable device such as the IND 112, this is meant only by way of example and not limitation. It is within the contemplation of the present inventors and within the scope of this document, that the systems, devices, and methods discussed herein may also be used for pain management via subcutaneous medical devices, wearable medical devices (e.g., wrist watch, patches, garment- or shoe-mounted device, etc.), or other external medical devices, or a combination of implantable, wearable, or other external devices. The therapy, such as electrostimulation or medical therapies, may be used to treat various neurological disorders other than pain, which by way of example and not limitation may include epilepsy, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. The external system 130 may be configured to control the operation of the IND 112, such as to program the IND 112 for delivering neuromodulation therapy. The external system 130 may additionally receive via the communication link 120 information acquired by IND 112, such as one or more sensor signal indicative of muscle tension. In an example, the external system 130 may determine a pain score based on the physiological or functional signals received from the IND 112, and program the IND 112 to deliver pain therapy in a closed-loop fashion. Examples of the external system and neurostimulation based on pain score are discussed below, such as with reference to FIGS. 2-3.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 112 and the external system 130. The transmitted data may include, for example, real-time sensor signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a hand-held external remote control device to remotely instruct the IND 112 to generate electrical stimulation pulses in accordance with selected stimulation parameters produced by the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
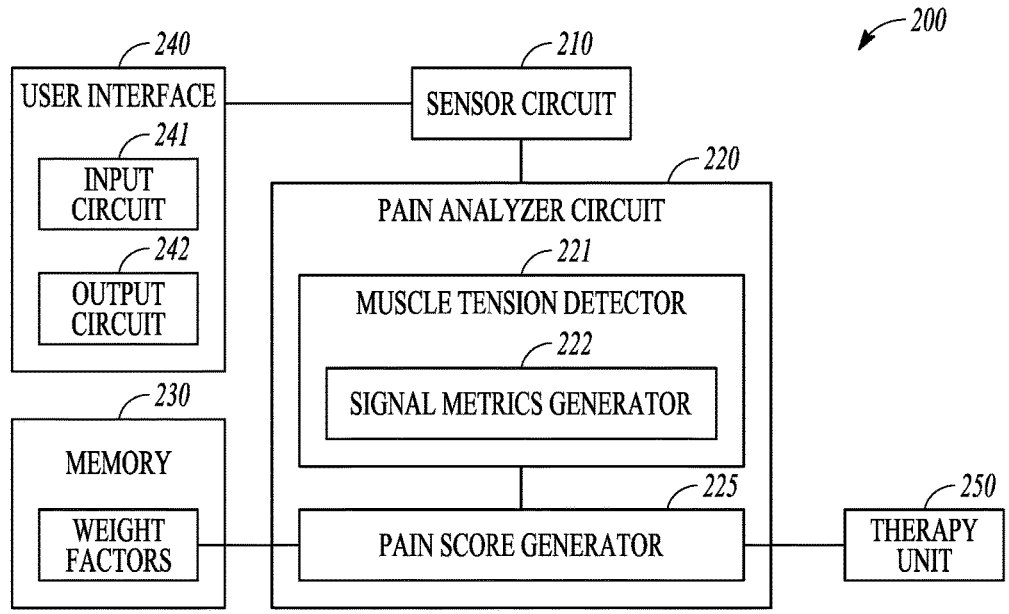
FIG. 2 illustrates, by way of example and not limitation, a block diagram of a pain management system.

FIG. 2 illustrates, by way of example and not limitation, an example of a pain management system 200, which may be an embodiment of the neuromodulation system 100. The pain management system 200 may assess pain in a subject using physiological signals that indicate the patient muscle tension, and program pain therapy based on the pain assessment. As illustrated in FIG. 2, the pain management system 200 may include a sensor circuit 210, a pain analyzer circuit 220, a memory 230, a user interface 240, and a therapy unit 250.

The sensor circuit 210 may be coupled to electrodes or various types of ambulatory sensors associated with the patient to sense one or more physiological signals from the patient. The sensor circuit 210 may include sense amplifier circuit that may pre-process the sensed physiological signals, including, for example, amplification, digitization, filtering, or other signal conditioning operations. Various physiological signals, such as cardiac, pulmonary, neural, or biochemical signals may demonstrate characteristic signal properties in response to an onset, intensity, severity, duration, or patterns of pain. In an example, the sensor circuit 210 may be coupled to implantable or wearable sensors to sense cardiac signals such as electrocardiograph (ECG), intracardiac electrogram, gyrocardiography, magnetocardiography, heart rate signal, heart rate variability signal, cardiovascular pressure signal, or heart sounds signal, among others. In another example, the sensor circuit 210 may sense pulmonary signals such as a respiratory signal, a thoracic impedance signal, or a respiratory sounds signal. In yet another example, the sensor circuit 210 may sense biochemical signals such as blood chemistry measurements or expression levels of one or more biomarkers, which may include, by way of example and not limitation, B-type natriuretic peptide (BNP) or N-terminal pro b-type natriuretic peptide (NT-proBNP), serum cytokine profiles, P2X4 receptor expression levels, gamma-aminobutyric acid (GABA) levels, TNFα and other inflammatory markers, cortisol, adenosine, Glial cell-derived neurotrophic factor (GDNF), Nav 1.3, Nav 1.7, or Tetrahydrobiopterin (BH4) levels, among other biomarkers.

In an example, the sensor circuit 210 may sense at least one signal indicative of muscle electrical or mechanical activity at a specific body location, such as electromyography (EMG) or a mechanical contraction signal. The muscle electrical or mechanical activity signal may contain information corresponding to muscle tension. Muscle tension and stiffness may contribute to pain in shoulder, neck, upper back, hips, upper and lower legs and feet. Information corresponding to muscle tension may be used to characterize and quantify patient pain. Examples of sensing muscle tensions signals are discussed below, such as with reference to FIG. 4.

The pain analyzer circuit 220 may generate a pain score based on the received physiological or functional signals indicative of muscle tension. The pain analyzer circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The pain analyzer circuit 220 may include circuit sets comprising one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the pain analyzer circuit 220 may include a muscle tension detector 221 and a pain score generator 225. The muscle tension detector 221 may include a signal metrics generator 222 configured to generate one or more signal metrics from the sensed physiological or functional signal. These signal metrics, hereinafter referred to as muscle tension signal metrics, may include statistical parameters extracted from the sensed signal, such as signal mean, median, or other central tendency measures or a histogram of the signal intensity, among others. The muscle tension signal metrics may additionally or alternatively include morphological parameters such as maximum or minimum within a specified time period such as a cardiac cycle, positive or negative slope or higher order statistics, or signal power spectral density at a specified frequency range, among other morphological parameters. The muscle tension signal metrics may additionally include timing information such as a time interval between a first characteristic point in one signal and a second characteristic point in another signal. The muscle tension signal metrics may be used to quantify the pain suffered by the patient. Examples of the signal metrics for pain quantification are discussed below, such as with reference to FIG. 4.

The pain score generator 225 may generate a pain score using the measurements of the signal metrics. The pain score can be represented as a numerical or categorical value that quantifies the patient's overall pain symptom. In an example, a composite signal metric may be generated using a combination of a plurality of the signal metrics weighted by their respective weight factors. The pain score generator 225 may compare the composite signal metric to one or more threshold values or range values, and assign a corresponding pain score (such as numerical values from 0 to 10) based on the comparison.

In another example, the pain score generator 225 may compare the signal metrics to their respective threshold values or range values, assign corresponding signal metric-specific pain scores based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others. The pain score generated by the pain score generator 225 may be output to a system user or a process.

In various examples, in addition to the physiological signals such as muscle electrical or mechanical activity signal, the sensor circuit 210 may sense one or more functional signals from the patient. Examples of the functional signals may include, but not limited to, patient posture, gait, balance, or physical activity signals, among others. The sensor circuit 210 may sense the functional signals via one or more implantable or wearable motion sensors, including an accelerometer, a gyroscope (which may be a one-, two-, or three-axis gyroscope), a magnetometer (e.g., a compass), an inclinometer, a goniometer, a electromagnetic tracking system (ETS), or a global positioning system (GPS) sensor, among others. Detailed description of functional signals for use in pain characterization are disclosed in commonly assigned U.S. Provisional Patent Application Ser. No. 62/445,075, entitled "PAIN MANAGEMENT BASED ON FUNCTIONAL MEASUREMENTS", the disclosures of which are incorporated herein by reference. The signal metrics generator 221 may generate functional signal metrics from functional signals, and the pain score generator 225 may determine the pain score using a linear or nonlinear combination of the muscle tension signal metrics and the functional signal metrics. Commonly assigned U.S. Provisional Patent Application Ser. No. 62/445,053, entitled "PAIN MANAGEMENT BASED ON CARDIOVASCULAR PARAMETERS" describes cardiovascular parameters such as arterial pulsatile activity and electrocardiography for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,069, entitled "PAIN MANAGEMENT BASED ON RESPIRATION-MEDIATED HEART RATES" describes information of respiration-mediated heart rate for use in pain analysis, the disclosure of which is incorporated herein by reference in its entirety. Commonly assigned U.S. Provisional Patent Application Ser. No. 62/445,082, entitled "PAIN MANAGEMENT BASED ON EMOTIONAL EXPRESSION MEASUREMENTS" describes measurements of patient emotional expressions for use in pain analysis, the disclosure of which is incorporated herein by reference in its entirety. One or more of these additional signals or measurements may be used by the pain analyzer circuit 220 to generate a pain score.

The memory 230 may be configured to store sensor signals or signal metrics such as generated by the sensor circuit 210 and the muscle tension detector 221, and the pain scores such as generated by the pain score generator 225. Data storage at the memory 230 may be continuous, periodic, or triggered by a user command or a specified event. In an example, as illustrated in FIG. 2, the memory 230 may store weight factors, which may be used by the pain score generator 225 to generate the pain score. The weight factors may be provided by a system user, or alternatively be automatically determined or adjusted such as based on the corresponding signal metrics' reliability in representing an intensity of the pain. Examples of the automatic weight factor generation are discussed below, such as with reference to FIG. 3.

The user interface 240 may include an input circuit 241 and an output unit 242. In an example, at least a portion of the user interface 240 may be implemented in the external system 130. The input circuit 241 may enable a system user to program the parameters used for sensing the physiological signals, generating signal metrics, or generating the pain score. The input circuit 241 may be coupled to one or more input devices such as a keyboard, on-screen keyboard, mouse, trackball, touchpad, touch-screen, or other pointing or navigating devices. In some example, the input circuit may be incorporated in a mobile device such as a smart phone or other portable electronic device with a mobile application ("App"). The mobile App may enable a patient to provide pain description or quantified pain scales during the pain episodes. In an example, the input circuit 241 may enable a user to confirm, reject, or edit the programming of the therapy unit 250, such as parameters for electrostimulation, as to be discussed in the following.

The output unit 242 may include a display to present to a system user such as a clinician the pain score. The output unit 242 may also display information including the physiological and functional signals, trends of the signal metric, or any intermediary results for pain score calculation such as the signal metric-specific pain scores. The information may be presented in a table, a chart, a diagram, or any other types of textual, tabular, or graphical presentation formats, for displaying to a system user. The presentation of the output information may include audio or other human-perceptible media format. In an example, the output unit 242 may generate alerts, alarms, emergency calls, or other forms of warnings to signal the system user about the pain score.

The therapy circuit 250 may be configured to deliver a therapy to the patient based on the pain score generated by the pain score generator 225. In an example, the therapy circuit 250 may include an electrostimulator configured to generate electrostimulation energy to treat pain. In an example, the electrostimulator may deliver spinal cord stimulation (SCS) via electrodes electrically coupled to the electrostimulator. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator may additionally or alternatively deliver electrostimulation to other target tissues such as peripheral nerves tissues. In an example, the electrostimulator may deliver transcutaneous electrical nerve stimulation (TENS) via detachable electrodes that are affixed to the skin.

The therapy circuit 250 may additionally or alternatively include a drug delivery system, such as an intrathecal drug delivery pump that may be surgically placed under the skin, which may be programmed to inject medication or biologics through a catheter to the area around the spinal cord. Other examples of drug delivery system may include a computerized patient-controlled analgesia pump that may deliver the prescribed pain medication to the patient such as via an intravenous line. In some examples, the therapy circuit 250 may be delivered according to the pain score received from the pain score generator 225.

Figure 3:
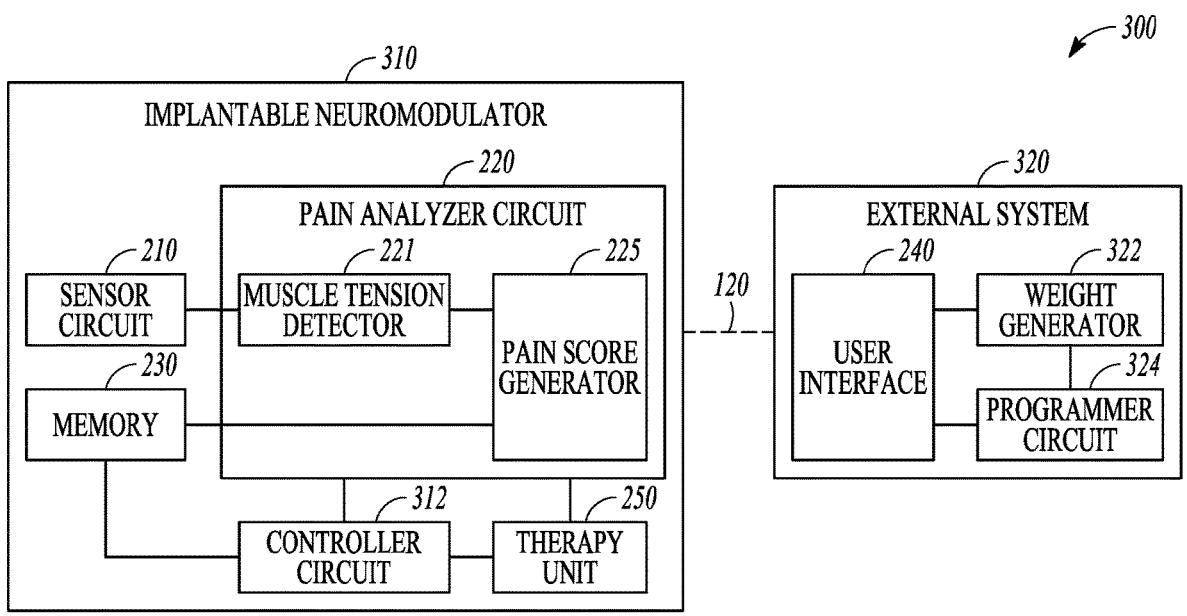
FIG. 3 illustrates, by way of example and not limitation, a block diagram of another pain management system.

FIG. 3 illustrates, by way of example and not limitation, another example of a pain management system 300, which may be an embodiment of the neuromodulation system 100 or the pain management system 200. The pain management system 300 may include an implantable neuromodulator 310 and an external system 320, which may be, respectively, embodiments of the IND 112 and the external system 130 as illustrated in FIG. 1. The external system 320 may be communicatively coupled to the implantable neuromodulator 310 via the communication link 120.

The implantable neuromodulator 310 may include several components of the pain management system 200 as illustrated in FIG. 2, including the sensor circuit 210, the pain analyzer circuit 220, the memory 230, and the therapy unit 250. As discussed with reference to FIG. 2, the pain analyzer circuit 220 includes the pain score generator 225 that determines a pain score using weight factors stored in the memory 230 and the signal metrics from the muscle tension detector 221 which may also be included in the pain analyzer circuit 220. The implantable neuromodulator 310 may include a controller circuit 312, coupled to the therapy unit 250, which controls the generation and delivery of pain therapy, such as neurostimulation energy. The controller circuit 312 may control the generation of electrostimulation pulses according to specified stimulation parameters. The stimulation parameters may be provided by a system user. Alternatively, the stimulation parameters may be automatically determined based on the intensity, severity, duration, or pattern of pain, which may be subjectively described by the patient or automatically quantified based on the physiological or functional signals sensed by the sensor circuit 210. For example, when a patient-described or sensor-indicated quantification exceeds a respective threshold value or falls within a specified range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specified range indicating no pain or mild pain, the electrostimulation energy may be decreased. The controller circuit 312 may also adjust stimulation parameters to alleviate side effects introduced by the electrostimulation of the target tissue.

Additionally or alternatively, the controller circuit 312 may control the therapy unit 250 to deliver electrostimulation pulses via specified electrodes. In an example of pain management via SCS, a plurality of segmented electrodes, such as the electrodes 116, may be distributed in one or more leads. The controller circuit 312 may configure the therapy unit 250 to deliver electrostimulation pulses via a set of electrodes selected from the plurality of electrodes. The electrodes may be manually selected by a system user, or automatically selected based on the pain score.

The implantable neuromodulator 310 may receive the information about electrostimulation parameters and the electrode configuration from the external system 320 via the communication link 120. Additional parameters associated with operation of the therapy unit 250, such as battery status, lead impedance and integrity, or device diagnostic of the implantable neuromodulator 310, may be transmitted to the external system 320. The controller circuit 312 may control the generation and delivery of electrostimulation using the information about electrostimulation parameters and the electrode configuration from the external system 320. Examples of the electrostimulation parameters and electrode configuration may include: temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst; or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, the controller circuit 312 may control the generation and delivery of electrostimulation in a closed-loop fashion by adaptively adjusting one or more stimulation parameters or stimulation electrode configuration based on the pain score. For example, if the score exceeds the pain threshold (or falls within a specified range indicating an elevated pain), then the first electrostimulation may be delivered. Conversely, if the multi-sensor pain score falls below a respective threshold value (or falls within a specified range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In an example, the first electrostimulation may have higher energy than the second electrostimulation, such as to provide stronger effect of pain relief. Examples of increased electrostimulation energy may include higher pulse intensity, a higher frequency, a longer stimulation duration or "on" cycle, among others.

The parameter adjustment or stimulation electrode configuration may be executed continuously, periodically at specified time, duration, or frequency, or in a commanded mode upon receiving from a system user a command or confirmation of parameter adjustment. In an example, adjustment of stimulation parameter or electrode configuration may be performed during implant of a stimulation lead (e.g., a SCS lead) to optimize electrode location and stimulation parameters to achieve desired therapeutic outcome. The muscle tension signal may be measured using sensors or electrodes disposed at pain locations while pain stimulation is delivered. Because muscle tension-based pain characterization does not require patient subjective indication of pain relief, lead placement and muscle tension measurement may be carried out while patient is asleep. In some examples, the closed-loop control of the electrostimulation may be further based on the type of the pain, such as chronic or acute pain. In an example, the pain analyzer circuit 220 may trend the signal metric over time to compute an indication of abruptness of change of the signal metrics, such as a rate of change over a specified time period. The pain episode may be characterized as acute pain if the signal metric changes abruptly (e.g., the rate of change of the signal metric exceeding a threshold), or as chronic pain if the signal metric changes gradually (e.g., the rate of change of the signal metric falling below a threshold). The controller circuit 312 may control the therapy unit 250 to deliver, withhold, or otherwise modify the pain therapy in accordance with the pain type. For example, incidents such as toe stubbing or bodily injuries may cause abrupt changes in certain signal metrics, but no adjustment of the closed-loop pain therapy is deemed necessary. On the contrary, if the pain analyzer circuit 220 detects chronic pain characterized by gradual signal metric change, then the closed-loop pain therapy may be delivered accordingly.

The external system 320 may include the user interface 240, a weight generator 322, and a programmer circuit 324. The weight generator 322 may generate weight factors used by the pain score generator 225 to generate the pain score. The weight factors may indicate the signal metrics' reliability in representing an intensity of the pain. A sensor metric that is more reliable, or more sensitive or specific to the pain, would be assigned a larger weight than another sensor metric that is less reliable, or less sensitive or specific to the pain. In an example, the weight factors may be proportional to correlations between a plurality of quantified pain scales (such as reported by a patient) and measurements of the measurements of the signal metrics corresponding to the plurality of quantified pain scales. A signal metric that correlates with the pain scales is deemed a more reliable signal metric for pain quantification, and is assigned a larger weight factor than another signal metric less correlated with the quantified pain scales. In another example, the weight generator 322 may determine weight factors using the signal sensitivity to pain. The signal metrics may be trended over time, such as over approximately six months. The signal sensitivity to pain may be represented by a rate of change of the signal metrics over time during a pain episode. The signal sensitivity to pain may be evaluated under a controlled condition such as when the patient posture or activity is at a specified level or during specified time of the day. The weight generator 322 may determine weight factors to be proportional to signal metric's sensitivity to pain.

The programmer circuit 324 may produce parameter values for operating the implantable neuromodulator 310, including parameters for sensing physiological and functional signals and generating signal metrics, and parameters or electrode configurations for electrostimulation. In an example, the programmer circuit 324 may generate the stimulation parameters or electrode configurations for SCS based on the pain score produced by the pain score generator 225. Through the communication link 120, the programmer circuit 324 may continuously or periodically provide adjusted stimulation parameters or electrode configuration to the implantable neuromodulator 210A. By way of non-limiting example and as illustrated in FIG. 3, the programmer circuit 324 may be coupled to the user interface 234 to allow a user to confirm, reject, or edit the stimulation parameters, sensing parameters, or other parameters controlling the operation of the implantable neuromodulator 210A. The programmer circuit 324 may also adjust the stimulation parameter or electrode configuration in a commanded mode upon receiving from a system user a command or confirmation of parameter adjustment.

The programmer circuit 324, which may be coupled to the weight generator 322, may initiate a transmission of the weight factors generated by the weight generator 322 to the implantable neuromodulator 310, and store the weight factors in the memory 230. In an example, the weight factors received from the external system 320 may be compared to previously stored weight factors in the memory 230. The controller circuit 312 may update the weight factors stored in the memory 230 if the received weight factors are different than the stored weights. The pain analyzer circuit 220 may use the updated weight factors to generate a pain score. In an example, the update of the stored weight factors may be performed continuously, periodically, or in a commanded mode upon receiving a command from a user. In various examples, weight factors may be updated using a fusion model. Commonly assigned U.S. Provisional Patent Application Ser. No. 62/445,095, entitled "PATIENT-SPECIFIC CALIBRATION OF PAIN QUANTIFICATION" describes systems and methods for calibrating a fusion model, such as adjusting weights for signal metrics, using a reference pain quantification, the disclosure of which is incorporated herein by reference in its entirety.

In some examples, the pain score may be used by a therapy unit (such as an electrostimulator) separated from the pain management system 300. In various examples, the pain management system 300 may be configured as a monitoring system for pain characterization and quantification without delivering closed-loop electrostimulation or other modalities of pain therapy. The pain characterization and quantification may be provided to a system user such as the patient or a clinician, or to a process including, for example, an instance of a computer program executable in a microprocessor. In an example, the process includes computer-implemented generation of recommendations or an alert to the system user regarding pain medication (e.g., medication dosage and time for taking a dose), electrostimulation therapy, or other pain management regimens. The therapy recommendations or alert may be based on the pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the pain score exceeding a threshold which indicates elevated pain symptom, an alert may be generated and presented at the user interface 240 to remind the patient to take pain medication. In another example, therapy recommendations or alerts may be based on information about wearing-off effect of pain medication, which may be stored in the memory 230 or received from the user interface 240. When the drug effect has worn off, an alert may be generated to remind the patient to take another dose or to request a clinician review of the pain prescription. In yet another example, before a pain therapy such as neurostimulation therapy is adjusted (such as based on the pain score) and delivered to the patient, an alert may be generated to forewarn the patient or the clinician of any impending adverse events. This may be useful as some pain medication may have fatal or debilitating side effects. In some examples, the pain management system 300 may identify effect of pain medication addiction such as based on functional and physiological signals. An alert may be generated to warn the patient about effects of medication addiction and thus allow medical intervention.

Figure 4:
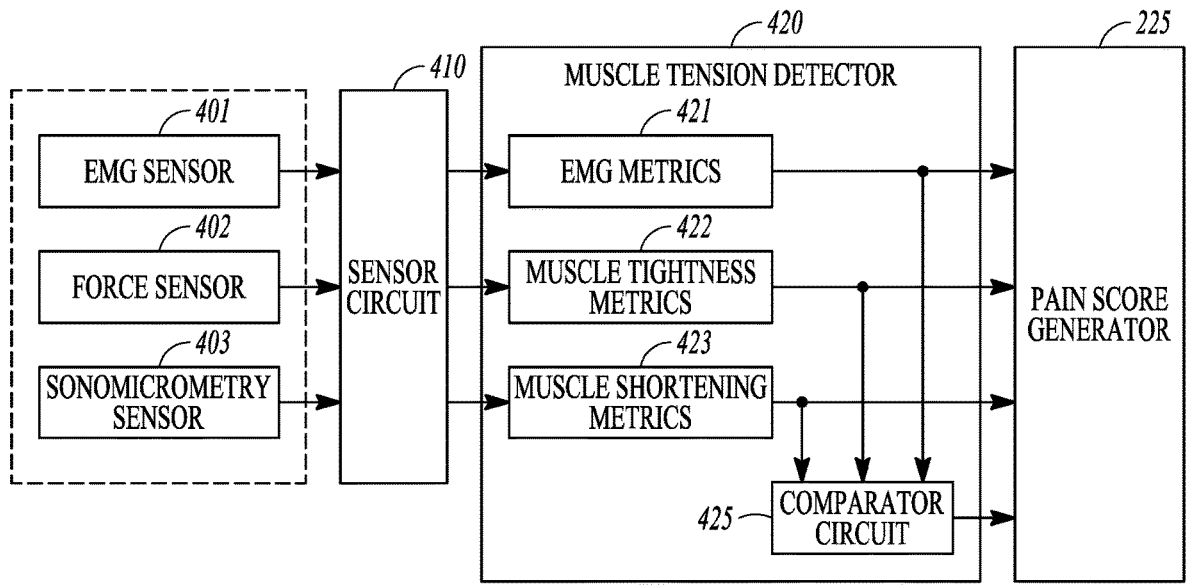
FIG. 4 illustrates, by way of example and not limitation, a portion of a pain management system for sensing signal indicative of muscle tension at a specific body location.

FIG. 4 illustrates, by way of example and not limitation, a portion of a pain management system for sensing signal indicative of muscle tension at a specific body location. The system portion may generate muscle tension signal metrics from one or more physiological or functional signals. The muscle tension signal metrics may be used by the pain management system 200 or 300 to characterize and quantify pain of a patient. The system portion may include one or more sensors 401 through 405, a sensor circuit 410 which is an embodiment of the sensor circuit 210, and a muscle tension detector 420 which is an embodiment of the signal metrics generator 221.

By way of example and not limitation, one or more of an electromyography (EMG) sensor 401, a force sensor 402, or a sonomicrometry sensor 403 may be used to measure muscle electrical or mechanical activities. The EMG sensor 401 may be configured to record electrical activity produced by skeletal muscles, which may include, by way of example and not limitation, rectus abdominis, internal oblique, external oblique, latissimus dorsi, iliocostalis lumborum, multifidus, corrugator supercilii group, or zygomaticus major muscle group, among others. In an example, the EMG sensors may be an implantable sensor with electrodes configured for subcutaneous placement at or near a target muscle. The electrode, such as a needle electrode, may be inserted within the muscle for intramuscular electrical activity recording or be placed above the muscle for supramuscular electrical activity recording. In another example, the EMG sensor may be a wearable sensor with surface electrodes or electrode patch configured to be directly placed on the skin of an area of target muscle. The EMG sensor may be worn on the head, shoulder, neck, chest, back, leg, arm, or other parts of the body. In some examples, the wearable EMG sensor may include epidermal sensors configured to be detachably mounted on a skin area of the specific body location of the patient. The epidermal sensors are mechanically flexible and stretchable devices that can conform to the microscale topology of the skin. Examples of epidermal sensors may include capacitive, biocompatible electrodes based on electrodes insulated with polydimethylsiloxane (PDMS) and skin adhesive patches that use biomimetic micropillars.

The EMG sensor 401 may record the EMG signal from a target muscle with known injury, tension, or stiffness contributing to pain. Additionally or alternatively, the EMG may be recorded from a muscle that is affected by pain, such as a muscle that overly contracts or repeatedly stretches to avoid pain sensation or to compensate for an injured muscle contributing to the pain.

In some examples, the EMG sensor 401 may record the EMG signal from a target muscle involved in patient emotional expression formation. Chronic pain may cause impaired cognitive function, emotional and psychological distress, depression, and motor control impairment. Some chronic pain patients may present with characteristic facial expressions, such as lowered brows, raised cheeks, tightened eyelids, a raised upper lip, an open mouth. Such characteristic facial expressions are controlled by, among other things, facial muscles. For example, corrugator supercilii muscle and procerus muscles are known to be major contributors to the facial expression of pain, and a contraction of the corrugator supercilii muscle and procerus muscles may produce characteristic facial expression of frowning or tightened eyelids. In an example, the EMG sensors may be positioned on the patient face to record an electrical activity of facial muscle tension associated with facial expression. A recording of facial muscle electrical activity may be correlated to and indicative of pain-associated emotional distress. Additionally or alternatively, the EMG sensors may be positioned on the patient cheek or neck to record an electrical activity of articulator muscle tension. Chronic pain may directly or indirectly cause abnormality in speech motor control, and result in characteristic patterns of vocal expression such as slower syllable pronunciation. The articulator muscles are muscles involved in speech sounds production, which may include one or more of jaw muscles (e.g., buccinators muscle and masseter muscle), laryngeal muscles, pharyngeal muscles, palatal muscles, among others. The speech sounds may be determined by, among other things, levels of muscle tension and changing muscle lengths and movements of structures. A recording of articulator muscle tension is associated with vocal expression, and may be correlated to and indicative of pain-associated emotional distress.

The force sensor 402 and sonomicrometry sensor 403 are, by way of example and not limitation, sensors that record mechanical contraction property of a muscle at the specified body location. The force sensor 402 may be configured to record force, or a parameter correlated to force, exerted by the muscle in tension. Examples of the force sensor 402 may include a strain gauge, a piezoelectric sensor, or a capacitive sensor, among others. The sonomicrometry sensor 403, which may include one or more sonomicrometry crystals, may be configured to measure muscle length change such as muscle shortening, which is indicative of muscle tension. In some examples, the sensor circuit 410 may be coupled to an impedance sensor to measure impedance change correlated to muscle tension. One or more of the force sensor 402, sonomicrometry sensor 403, or impedance sensors, among others, may be implantable, wearable, or otherwise ambulatory sensors associated with the patient and in communication with an ambulatory device such as the implantable neuromodulator 310. Other sensors, such as ultrasound and optical sensors, may be alternatively or additionally used for measuring muscle length.

The sensor circuit 410 may be coupled to one or more of the EGM sensor 401, the force sensor 402, or the sonomicrometry sensor 403 via a wired or wireless connection. Examples of the wireless connection may include a Bluetooth protocol, Ethernet, IEEE 802.11 wireless, an inductive telemetry link, or a radio-frequency telemetry link, among others. The sensor circuit 410 may include sense amplifier circuit that may pre-process the sensed functional signal. The muscle tension detector 420 may extract from the processed sensor signals a plurality of EMG metrics 421, muscle tightness metrics 422, or muscle shortening metrics 423. One or more of the signal metrics 421-423 may include time-domain features such as signal magnitude or variance, frequency-domain features such as power spectra at specified frequency bands, spectral entropy, frequency modulation of speech, or other transformed-domain features such as obtained from wavelet decomposition or speech signal filtering through a filter bank. In some examples, the feature extraction and recognition may include reducing the feature dimensionality through feature space projection such as a principal component analysis (PCA). The one or more of the signal metrics 421-423 may be forwarded to the pain score generator 225 to generate a composite pain score, as discussed previously with reference to FIGS. 2-3.

As illustrated in FIG. 4, the muscle tension detector 420 may include a comparator circuit 425 configured to detect muscle tension based on a comparison between one or more muscle tension signal metrics to their respective threshold values. In an example, a muscle tension is detected if one or more muscle tension signal metrics exceed their respective threshold values by a specified margin, or fall within respective value range. The detection of muscle tension may indicate occurrence of a pain episode or aggravation of pain, and may be used to trigger pain score generation, alert to a clinician, or a therapy administration. In an example, the pain score generator 225 may generate a composite pain score using one or more of the signal metrics 421-423 in response to a detection of the muscle tension.

In some patients, pain may cause asymmetric tension distribution at one or more muscles. Detection of such a bilateral asymmetry in muscle activity may provide an indicator of pain. In some examples, muscle tension sensors (such as one or more of the sensors 401-403) may be placed at two different positions of a muscle, such as an extensor, a flexor, or an oblique muscle contributing to back pain. In an example, a first muscle tension sensor is configured to be positioned at a first body position to sense muscle tension at one side of the muscle, and a second muscle tension sensor is configured to be positioned at a second body location to sense muscle tension at an opposite side of the muscle. The muscle tension signal metrics, such as one or more of the EMG metrics 421, muscle tightness metrics 422, or muscle shortening metrics 423, may be generated respectively for the first and second muscle tension signals. The comparator circuit 425 may compare the muscle tension signal metrics corresponding to different muscle sides, and detect a bilateral asymmetry indicator. The score generator 225 may generate a composite pain score further using the detected bilateral asymmetry indicator.

Figure 5:
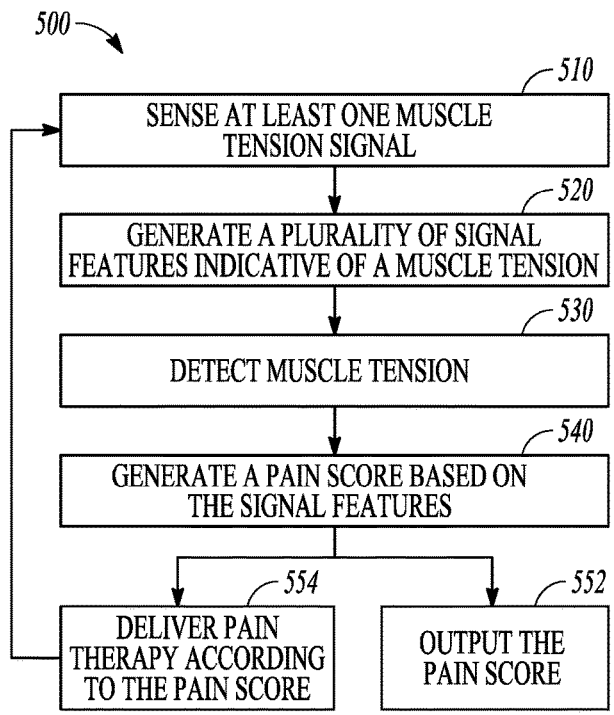
FIG. 5 illustrates, by way of example and not limitation, a method for managing pain of a patient.

FIG. 5 illustrates, by way of example and not limitation, a method 500 for managing pain of a patient. The method 500 may be implemented in a medical system, such as the pain management system 200 or 300. In an example, at least a portion of the method 500 may be executed by a neuromodulator device (IND) such as the implantable neuromodulator 310. In an example, at least a portion of the method 500 may be executed by an external programmer or remote server-based patient management system, such as the external system 320 that are communicatively coupled to the IND. The method 500 may be used to provide neuromodulation therapy to treat chronic pain or other disorders.

The method 500 begins at step 510, where various physiological signals, such as cardiac, pulmonary, neural, or biochemical signals may be detected using one or more physiological sensors. The physiological signals may contain information indicating onset, intensity, severity, duration, or patterns of pain. The sensed physiological signals may include at least one signal indicative of muscle electrical or mechanical activity at a specific body location. Chronic pain may be associated with muscle tension. Muscle tension and stiffness may also contribute to pain in shoulder, neck, upper back, hips, upper and lower legs and feet. Monitoring patient muscle tension may provide an objective assessment of pain, and may be used to improve pain therapy efficacy. In an example, the muscle electrical or mechanical activity signal may include an electromyography (EMG) signal recorded using a biopotential sensor such as the EMG sensor 401. The EMG sensor may include an implantable sensor, a wearable sensor, or an epidermal sensor. The EGM signal may be recorded from target muscle with known injury, tension, or stiffness contributing to pain. Additionally or alternatively, the EMG signal may be recorded from a muscle that is affected by pain, such as a muscle that overly contracts or repeatedly stretches to avoid pain sensation or to compensate for an injured muscle contributing to the pain. Examples of the target muscles for recording the EMG may include, by way of example and not limitation, rectus abdominis, internal oblique, external oblique, latissimus dorsi, iliocostalis lumborum, multifidus, corrugator supercilii group, or zygomaticus major muscle group, among others.

In an example, the EMG signal may be recorded from one or more facial muscles (e.g., corrugator supercilii muscle and procerus muscle) that contribute to facial expression formation. In another example, the EMG signal may be recorded from one or more articulator muscles (e.g., buccinators muscle and masseter muscle, laryngeal muscles, pharyngeal muscles, palatal muscles) that are involved in voice or speech sound production. Chronic pain may be associated with characteristic emotional expressions including patient facial and vocal expressions. The EMG measured from facial muscles and articulator muscles may be correlated to and indicative of pain-associated emotional distress.

In another example, the muscle tension signal may include a mechanical contraction signal, which may include a muscle force signal such as sensed using the force sensor 402, or a measure of muscle length or a change of muscle length (e.g., muscle shortening) such as sensed using the sonomicrometry sensor 403.

In some examples, in addition to the muscle tension signals, one or more other physiological or functional signals may also be sensed at 510. Examples of the physiological signals may include an electrocardiograph (ECG) or intracardiac electrogram, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others.

At 520, a plurality of signal metrics may be generated from the sensed muscle tension signals. The signal metrics may be indicative of muscle tension. Examples of the signal metrics may include EMG metrics, muscle tightness metrics, or muscle shortening metrics. The signal metrics may include statistical, morphological, or temporal metrics. Metrics of muscle tension may include time-domain features such as signal magnitude or variance, frequency-domain features such as power spectra at specified frequency bands, spectral entropy, frequency modulation of speech, or other transformed-domain features such as obtained from wavelet decomposition or speech signal filtering through a filter bank. In some examples, the signal metrics may be projected onto specific direction on the feature space for dimensionality reduction, such as by using principal component analysis (PCA).

At 540, muscle tension is detected using the plurality of signal features indicative of muscle tension. The muscle tension may be detected based on a comparison between one or more muscle tension signal metrics to their respective threshold values. In an example, a muscle tension is detected if one or more muscle tension signal metrics exceed their respective threshold values by a specified margin, or fall within respective value range. The detection of muscle tension may indicate occurrence of a pain episode or aggravation of pain, and may be used to trigger pain score generation, alert to a clinician, or a therapy administration. In an example, muscle tension may be detected based on a bilateral asymmetry in muscle activity. A first muscle tension signal may be sensed using a first sensor positioned at one side of a specific muscle. A second muscle tension signal may be sensed using a second sensor positioned at an opposite side the specific muscle. A bilateral asymmetry indicator may be generated such as based on a comparison of signal features respectively generated from the first and second muscle tension signals. The bilateral asymmetry indicator indicates asymmetric muscle activities between the one side and the opposite side of the specific muscle, which may be indicative of patient pain.

At 550, a pain score may be generated using the measurements of the signal metrics. The pain score may be generated using a combination of a plurality of signal metrics indicative of muscle tension. In some examples, one or more signal metrics generated from other physiological or functional signals may additionally be used to generate the pain score. The pain score may be represented as a numerical or categorical value that quantifies overall pain quality in the subject. In an example, a composite signal metric may be generated using a linear or nonlinear combination of the signal metrics respectively weighted by weight factors. The composite signal metric may be categorized as one of a number of degrees of pain by comparing the composite signal metric to one or more threshold values or range values, and a corresponding pain score may be assigned based on the comparison.

In another example, signal metrics may be compared to their respective threshold values or range values and corresponding signal metric-specific pain scores may be determined. A composite pain score may be generated using a linear or nonlinear fusion of the signal metric-specific pain scores weighted by their respective weight factors. Examples of the fusion algorithm may include decision trees, voting, weighted averages, or neural networks, among others. In some examples, the pain score may be computed using a subset of the signal metrics selected based on their temporal profile of pain response. Signal metrics with quick pain response (or a shorter transient state of response) may be selected to compute the pain score during a pain episode. Signal metrics with slow or delayed pain response (or a longer transient state of response before reaching a steady state) may be used to compute the pain score after an extended period following the onset of pain such as to allow the signal metrics to reach steady state of response. In some examples, patient demographic information such as patient age or gender may be used in computing the pain score. A higher pain threshold for the composite signal metric may be selected for male patients than for female patients. Additionally or alternatively, the respective weight factors may be determined based on patient demographic information. The weight factors for the signal metrics may be tuned to a lower value than the weight factors for the same signal metric in a female patient.

At 552, the pain score may be output to a user or to a process, such as via the output unit 242 as illustrated in FIG. 2. The pain score, including the composite pain score and optionally together with metric-specific pain scores, may be displayed on a display screen. Other information, such as the facial image or video sequence or recorded voice or speech, and the signal metrics generated therefrom, may also be output for display or for further processing. In some examples, alerts, alarms, emergency calls, or other forms of warnings may be generated to signal the system user about occurrence of a pain episode or aggravation of pain as indicated by the pain score.

The method 500 may include, at 554, an additional step of delivering a pain therapy to the patient according to the pain score. The pain therapy may include electrostimulation therapy, such as spinal cord stimulation (SCS) via electrodes electrically coupled to the electrostimulator. The SCS may be in a form of stimulation pulses that are characterized by pulse amplitude, pulse width, stimulation frequency, duration, on-off cycle, waveform, among other stimulation parameters. Other electrostimulation therapy, such as one or a combination of DBS, FES, VNS, TNS, or PNS at various locations, may be delivered for pain management. The pain therapy may additionally or alternatively include a drug therapy such as delivered by using an intrathecal drug delivery pump.

In various examples, the pain therapy (such as in the form of electrostimulation or drug therapy) may be delivered in a closed-loop fashion. Therapy parameters, such as stimulation waveform parameters, stimulation electrode combination and fractionalization, drug dosage, may be adaptively adjusted based at least on the pain score. The pain-relief effect of the delivered pain therapy may be assessed based on the signal metrics such as the cardiovascular parameters, and the therapy may be adjusted to achieve desirable pain relief. The therapy adjustment may be executed continuously, periodically at specified time, duration, or frequency, or in a commanded mode upon receiving from a system user a command or confirmation of parameter adjustment. In an example, if the pain score exceeds the pain threshold (or falls within a specified range indicating an elevated pain), then the first electrostimulation may be delivered. Conversely, if the composite pain score falls below a respective threshold value (or falls within a specified range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. The method 500 may proceed at 510 to sense muscle tension signals in response to the therapy delivered at 544. In some examples, the responses of the signal metrics to pain therapy delivered at 544 may be used to gauge composite pain score computation such as by adjusting the weight factors. In an example, weight factors may be determined and adjusted via the weight generator 322 as illustrated in FIG. 3, to be proportional to signal metric's sensitivity to pain.

Figure 6:
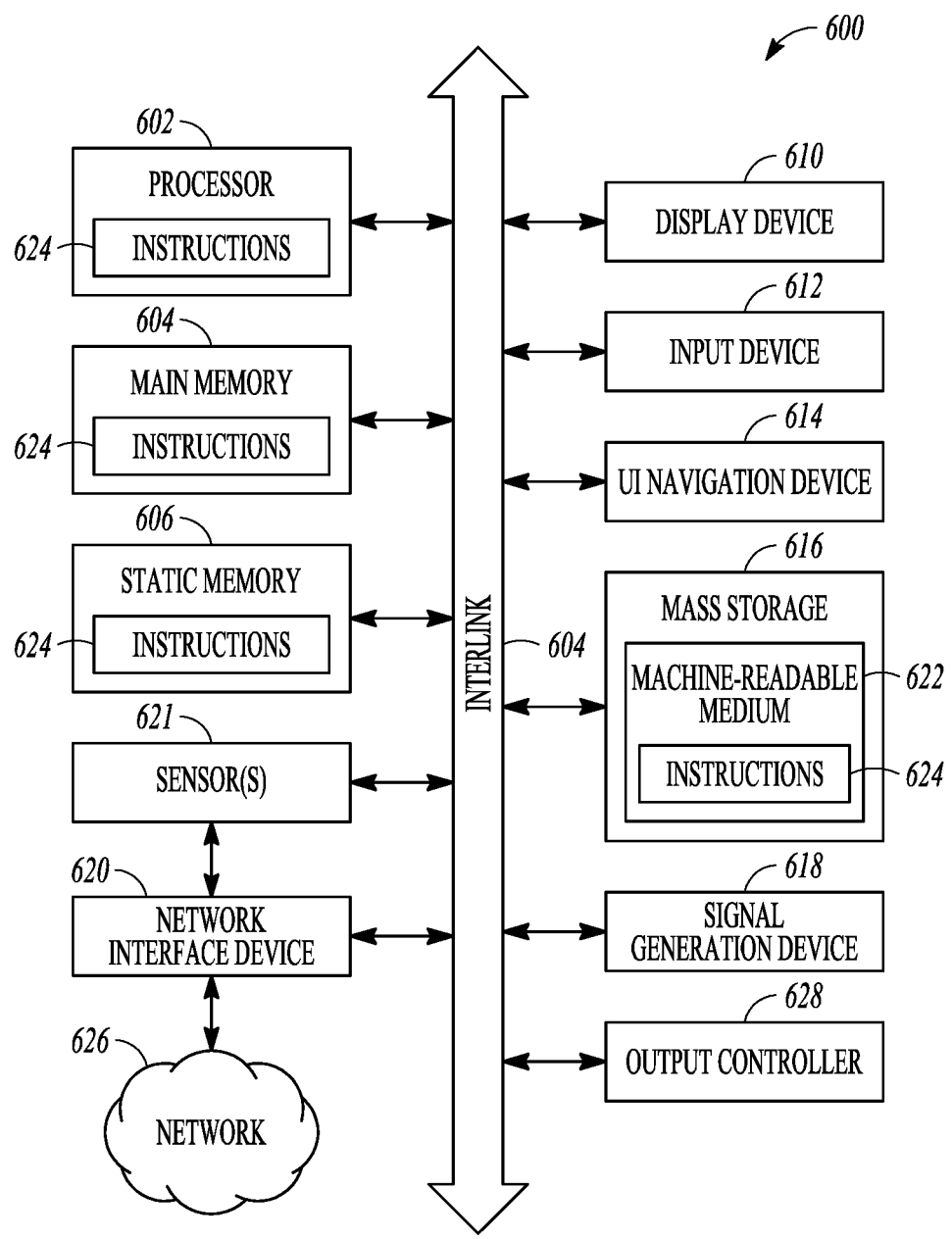
FIG. 6 illustrates, by way of example and not limitation, a block diagram of an example machine upon which any one or more of the techniques discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for managing pain of a patient, the system comprising:
   a sensor circuit coupled to one or more sensors configured to sense from the patient at least one muscle mechanical contraction signal at a specific body location;
   a pain analyzer circuit coupled to the sensor circuit, the pain analyzer circuit configured to:
   detect muscle tension using one or more signal metrics generated from the sensed at least one muscle mechanical contraction signal at the specific body location; and
   generate a pain score using the generated one or more signal metrics; and
   an output unit configured to output the pain score to a user or a processing device.

2. The system of claim 1, further comprising:
   an electrostimulator configured to generate electrostimulation energy to treat pain; and
   a controller circuit coupled to the pain analyzer circuit and the electrostimulator, the controller circuit configured to control the electrostimulator to deliver a pain therapy and to control the electrostimulation energy generated by the electrostimulator according to the pain score.

3. The system of claim 2, wherein the electrostimulator is further configured to deliver at least one of:
   a spinal cord stimulation;
   a brain stimulation;
   or a peripheral nerve stimulation.

4. The system of claim 2, wherein the controller circuit is further configured to deliver first electrostimulation to the patient in response to the pain score exceeding a threshold value, and to deliver second electrostimulation to the patient in response to the pain score falling below the threshold value;
   wherein the first and second electrostimulations differ in at least one of an electrostimulation energy, an electrostimulation pulse shape, or an electrostimulation pattern.

5. The system of claim 2, further comprising an implantable neuromodulator device (IND) that includes one or more of the sensor circuit, the pain analyzer circuit, or the electrostimulator.

6. The system of claim 1, wherein the sensor circuit is coupled to an electromyography (EMG) sensor configured to sense an EMG signal at the specific body location.

7. The system of claim 1, wherein the sensor circuit is coupled to a force sensor configured to measure a muscle force parameter at the specific body location of the patient.

8. The system of claim 1, wherein the sensor circuit is coupled to a sonomicrometry crystal configured to record muscle shortening.

9. The system of claim 1, wherein:
   the sensor circuit is coupled to first and second sensors, the first sensor configured to be positioned at a first patient location to sense a first muscle tension signal at one side of a specific muscle, and the second sensor configured to be positioned at a second patient location to sense a second muscle tension signal at an opposite side of the specific muscle; and
   the pain analyzer circuit is further configured to:
   detect a bilateral asymmetry indicator using first signal metrics generated from the first muscle tension signal and second signal metrics generated from the second muscle tension signal, the bilateral asymmetry indicator indicating asymmetric muscle activities between the one side and the opposite side of the specific muscle; and
   generate the pain score further using the detected bilateral asymmetry indicator.

10. The system of claim 1, wherein the pain analyzer circuit is further configured to generate the pain score using a combination of a plurality of the signal metrics weighted by their respective weight factors.

11. A method for managing pain of a patient using an implantable neuromodulator device (IND), the method comprising:
    sensing at least one muscle mechanical contraction signal at a specific body location of the patient using one or more sensors;
    generating, from the sensed at least one muscle mechanical contraction signal, one or more signal metrics indicative of muscle tension at the specific body location of the patient;
    detecting a muscle tension using the one or more signal metrics;
    generating a pain score based on the one or more signal metrics; and
    outputting the pain score to a user or a process.

12. The method of claim 11, further comprising delivering a pain therapy via the IND, the pain therapy including electrostimulation energy determined according to the pain score.

13. The method of claim 11, further comprising sensing an electromyography (EMG) signal from a patient skin area next to a target muscle, the EMG signal indicative of an electrical activity of muscle tension contributing to or affected by patient pain.

14. The method of claim 11, further comprising sensing an EMG signal from a face of the patient, the EMG signal indicative of an electrical activity of facial muscle tension associated with pain-related emotional distress.

15. The method of claim 11, wherein the muscle mechanical contraction signal includes information about muscle force or muscle shortening.

16. The method of claim 11, wherein:
sensing the muscle mechanical contraction signal includes sensing first and second muscle tension signals via respective first and second sensors, the first muscle tension signal indicative of a muscle tension at one side of a specific muscle, the second muscle tension signal indicative of a muscle a tension at an opposite side of the specific muscle;
detecting the muscle tension includes detecting a bilateral asymmetry indicator using first signal metrics generated from the first muscle tension signal and second signal metrics generated from the second muscle tension signal, the bilateral asymmetry indicator indicating asymmetric muscle activities between the one side and the opposite side of the specific muscle; and
generating the pain score further using the detected bilateral asymmetry indicator.

17. The method of claim 11, wherein generating the pain score includes using a combination of a plurality of the signal metrics weighted by their respective weight factors.

18. A non-transitory machine-readable storage medium, comprising a plurality of instructions that, responsive to being executed with processor circuitry of a computing device, cause the computing device to:
sense at least one muscle mechanical contraction signal at a specific body location of the patient using one or more sensors;
generate, from the sensed at least one muscle mechanical contraction signal, one or more signal metrics indicative of muscle tension at the specific body location of the patient;
detect a muscle tension using the one or more signal metrics;
generate a pain score based on the one or more signal metrics; and
output the pain score to a user or a processing device.

19. The non-transitory machine-readable storage medium of claim 18, wherein the instruction that causes the computing device to sense at least one muscle mechanical contraction signal includes an instruction causing the computing device to sense information about muscle force or muscle shortening.

20. The non-transitory machine-readable storage medium of claim 18, further comprising an instruction that causes the computing device to:
sense the muscle mechanical contraction signal including first and second muscle tension signals via respective first and second sensors, the first muscle tension signal indicative of a muscle tension at one side of a specific muscle, the second muscle tension signal indicative of a muscle a tension at an opposite side of the specific muscle;
detect the muscle tension includes detecting a bilateral asymmetry indicator using first signal metrics generated from the first muscle tension signal and second signal metrics generated from the second muscle tension signal, the bilateral asymmetry indicator indicating asymmetric muscle activities between the one side and the opposite side of the specific muscle; and
generate the pain score further using the detected bilateral asymmetry indicator.

* * * * *